United States Patent [19]

Wallace et al.

[11] Patent Number: 5,958,442
[45] Date of Patent: Sep. 28, 1999

[54] ONCOSTATIN M FOR TREATING INFLAMMATION

[75] Inventors: Philip M. Wallace, Seattle; Thomas J. Brown, Indianola, both of Wash.

[73] Assignee: Bristol-Myers Squibb Company, New York, N.Y.

[21] Appl. No.: 08/957,234

[22] Filed: Oct. 24, 1997

[51] Int. Cl.$^6$ .................................................... A61F 2/02
[52] U.S. Cl. ............................................................ 424/423
[58] Field of Search ............................................. 424/423

[56] References Cited

U.S. PATENT DOCUMENTS

| | | |
|---|---|---|
| 4,501,728 | 2/1985 | Geho et al. . |
| 4,837,028 | 6/1989 | Allen . |
| 4,975,282 | 12/1990 | Cullis et al. . |
| 5,428,012 | 6/1995 | Shoyab et al. . |
| 5,744,304 | 4/1998 | Munsford .................................. 435/6 |

OTHER PUBLICATIONS

Zarling et al., "Oncostatin M: A Growth Regulator Produced by Differentiated Histiocytic Lymphoma Cells," *PNAS* 83:9739–9743 (1986).

Malik et al., "Molecular Cloning, Sequence Analysis and Functional Expression of a Novel Growth Regulator, Oncostatin M," *Mol. Cell. Biol.* 9:2847–2853 (Jul., 1989).

Linsley et al., "Identification and Characterization of Cellular Receptors for the Growth Regulator, Oncostatin M," *J. Biol. Chem.* 264:4282–289 (1989).

Rose et al., "Oncostatin M is a Member of a Cytokine Family that Includes Leukemia–Inhibitory Factor, Granulocyte Colony–Stimulating Factor, and Interleukin 6," *PNAS* 88:8641–8645 (1991).

Gearing et al., "Oncostatin M Binds the High Affinity Leukemia Inhibitory Factor Receptor," *New Biol.*, 4:61–65 (1992).

Richards et al., "Recombinant Oncostatin M Stimulates the Production of Acute Phase Proteins in HepG2 Cells and Rat Primary Hepatocytes in Vitro," *J. Immunol.* 148:1731–1736 (1992).

Thoma et al., "Oncostatin M and Leukemia Inhibitory Factor Trigger Overlapping and Different Signals Through Partially Shared Receptor Complexes," *J. Biol. Chem.* 269:6215–6222 (1994).

Moseley et al., "Dual Oncostatin M (OSM) Receptors," *J. Biol. Chem.* 271:32635–43 (1996).

*Primary Examiner*—Carlos A. Azpuru
*Attorney, Agent, or Firm*—Townsend and Townsend and Crew LLP

[57] ABSTRACT

Oncostatin M is employed in methods to treat acute and chronic gastrointestinal inflammation, rheumatoid arthritis and multiple sclerosis.

12 Claims, 5 Drawing Sheets

ONCOSTATIN M FOR TREATING INFLAMMATION

BACKGROUND OF THE INVENTION

Oncostatin M (OM) is a pleiotropic cytokine produced late in the activation cycle of T-cells and macrophages. Initially reported in 1986 (Zarling et al., *Proc. Natl. Acad. Sci. U.S.A.* 83: 9739–9743 (1986)), Oncostatin M has been extensively characterized and numerous activities ascribed to it. It was originally isolated from conditioned media of a phorbol ester-treated histiocytic lymphoma cell line, U937, based on the ability to inhibit the growth or development of a human melanoma cell line. Cloning of a cDNA for Oncostatin M showed that it encodes a 227 amino acid polypeptide (Malik et al., *Mol. Cell. Biol.* 9: 2847–2853 (1989)) which is structurally and functionally related to the family of hematopoietic and neurotrophic cytokines whose members include leukemia inhibitory factor (LIF), interleukin-6 (IL-6), interleukin-11 (IL-11), ciliary neurotrophic factor (CNTF), and cardiotrophin. Rose and Bruce, *Proc. Natl. Acad. Sci. U.S.A.* 88: 8641–8645 (1991).

Oncostatin M has been found to bind to three cell surface receptors. It binds to a gp130 polypeptide, also known as the IL-6 signal transduction subunit, with a low affinity, but the interaction, by itself, appears to be nonfunctional (Gearing, *New Biol.*, 4:61 (1992)). In a second, intermediate affinity interaction, Oncostatin M and LIF have been shown to compete for binding to a receptor composed of the low-affinity LIF receptor and gp130. This intermediate affinity receptor complex is capable of signalling and exerting biological effects in vitro. Although this receptor complex is shared by the two cytokines, the affinity of interaction and biological signals delivered by each of the cytokines are distinct. The third receptor recognized by Oncostatin M is a high affinity receptor that is not known to bind to other cytokines. It is believed responsible for mediating those properties which are unique to Oncostatin M (Linsley et al., *J. Biol. Chem.* 264: 4282–289, (1989); Thomas et al.,*J. Biol. Chem.* 269: 6215–6222 (1994)). The high affinity Oncostatin M receptor is composed of gp130 and an affinity-converting subunit (Moseley et al., *J. Biol. Chem.* 271:32635–43 (1996)) that has been cloned. The affinity-converting subunit is required for high affinity and functional ligand-receptor binding.

The overlapping properties of the IL-6-like cytokines presumably arise from the presence of gp130 in each of their receptors. However, there are unique properties and signal transduction pathways which are engaged when these receptors bind their ligands. In vitro, Oncostatin M acts on a wide variety of cells and elicits a multitude of biological responses, including growth modulation, leukemia cell differentiation, LDL receptor up-regulation, stimulation of plasminogen activator, induction of hematopoietic factors, induction of acute phase proteins, inhibition of embryonic stem cell differentiation, and induction of tissue-inhibitors of metalloproteinases-1. Of these properties, many are shared with other related cytokines, though others as yet have only been ascribed to Oncostatin M.

The in vivo toxicology and pharmokinetics of Oncostatin M have been evaluated. Recombinant Oncostatin M expressed in CHO cells has been administered to normal or myelosuppressed mice without lethality and with minimal weight loss. Oncostatin M administered intravenously is rapidly (~10 minutes) cleared to the liver and kidney; at one hour <3% remains in these organs, suggesting that it is metabolized. Injection of mice with Oncostatin M results in increased levels of circulating platelets while there is no effect on red or white blood cell levels. A similar effect has been found in a non-human primate (i.e. cynmolgus and Rhesus monkey) where there is a dose-dependent increase in circulating platelet levels.

Oncostatin M has been reported to induce activity of acute phase proteins in hepatocytes (Richards et al., *J. Immunol.* 148:1731–1736 (1992), and thus has been proposed to be administered therapeutically to stimulate acute phase responses and treat disease states or injuries that result in either an inflammatory response or tissue degeneration at an afflicted site. Shoyab et al., PCT/US93/07326, incorporated herein by reference.

Inflammation occurs in response to numerous conditions including physical injury, tumor growth in a tissue, chemical damage to a tissue, and bacterial, parasitic, fungal or viral infection. Inflammation results in both local and systemic effects. Representative effects that can occur at a site of injury or disease are increased vascular permeability, release of degradative enzymes including metalloproteinase, migration to the affected site by leukocytes, neutrophil burst response to destroy invading cells, and the secretion of cytokines. Important systemic effects include pain, fever, and the acute phase response of the liver.

The acute phase response involves the production of a broad spectrum of substances acting, in general terms, to regulate the cells and enzymes that are responsible for inactivating the causative agent(s) of the inflammatory process. Thus, the acute phase proteins form a "feedback loop" that minimizes adventitious tissue damage and regulates the eventual return to homeostasis. The feedback process is pleiotropic and includes the production of anti-inflammatory cytokines, inhibitors of proinflammatory cytokines and inhibitors of numerous degradative proteases that are active in inflammation.

The temporal expression of cytokines reflects their respective roles during progression and resolution of an inflammatory response. TNF-alpha, for example, is rapidly induced following tissue injury or infection, triggering an inflammatory response that is amplified by the induction of IL-1-alpha and -beta. As feedback to limit and subsequently attenuate inflammation, IL-6, protease inhibitor proteins, and corticosterone are induced to shift the balance to wound repair and suppression of inflammation.

What is needed in the art is a means to control specific inflammatory conditions by enhancing the anti-inflammatory feedback loop. The process should work in conjunction with naturally occurring cytokines to enhance the negative feedback of proinflammatory cytokine production, in addition to inhibiting the biological effects of the proinflammatory molecules. Moreover, the therapeutic process should be capable of having a direct effect on epithelial cells and fibroblasts to minimize the inflammatory process surrounding these cells, particularly those epithelial cells of the synovium, lungs, and the gastrointestinal tract which are particularly susceptible to inflammatory disease and damage induced by radiation and cytotoxic cancer therapies. Quite surprisingly, the present invention addresses these and other related needs.

SUMMARY OF THE INVENTION

The present invention provides, in one embodiment, a method for inhibiting gastrointestinal inflammation in a mammalian host. According to this method a gastrointestinal inflammation-inhibiting amount of Oncostatin M is administered to the host. The host can be suffering from or susceptible to acute or chronic gastrointestinal inflammation, e.g., inflammatory bowel disease, Crohn's Disease or ulcerative colitis. Typically, the Oncostatin M is administered intravenously, but can be administered orally to treat gastrointestinal inflammation. The Oncostatin M is typically the human form of the molecule or a variant thereof when treatment is intended for humans. It can be expressed in a mammalian cell line, such as Chinese Hamster Ovary cells (CHO), or in yeast, such as a methylotrophic yeast species, e.g., Pichia.

In another aspect the invention provides a means for inhibiting rheumatoid arthritis in a mammalian host, especially a human, who is prone to rheumatoid arthritis or already suffering from the disease. The host is administered an amount of Oncostatin M sufficient to inhibit inflammation associated with one or more joints of the host, thereby inhibiting the rheumatoid arthritis. According to this method, the Oncostatin M is administered parenterally or orally, including administration at a specific site associated with the disease, e.g., joints or the like. The Oncostatin M is typically expressed in a mammalian cell line, yeast, etc.

In a further embodiment the invention provides a method for alleviating symptoms of multiple sclerosis in a host. The host receives an amount of Oncostatin M sufficient to inhibit neurological inflammation associated with multiple sclerosis, thereby alleviating symptoms of the disease. The Oncostatin M is administered either parenterally or orally so as to achieve sufficient levels in affected tissues. The pharmaceutical compositions comprising Oncostatin M, typically the human form of the molecule or variants or fragments thereof for this intended treatment, is expressed in a mammalian cell line, e.g., CHO, or the like.

TNF and IL-1 are primary mediators common to these diseases, upregulating proteases, esterases, and reactive oxygen that affect tissue destruction. Oncostatin M suppresses TNF production and IL-1 activity and induces inhibitors of protease/esterase and reactive oxygen, and acute phase proteins to attenuate inflammation and tissue destruction.

DETAILED DESCRIPTION OF THE SPECIFIC EMBODIMENTS

The present invention provides methods for treating a variety of specific conditions associated with inflammation using Oncostatin M (OM). In one embodiment of the invention, the condition is gastrointestinal inflammation, including both acute and chronic gastrointestinal inflammation. In another embodiment the condition is rheumatoid arthritis. Yet another disease is multiple sclerosis. For treatment purposes, compositions containing Oncostatin M are administered to a host predisposed to or already suffering from the condition. Oncostatin M acts to inhibit inflammation and tissue damage associated with the particular disease as well as other manifestations of the disease.

As used herein, the terms "treatment" or "treating" cover any treatment of the disease condition, and include: (1) preventing the disease from occurring in a subject who does not have the disease or who has not yet been diagnosed as having it; (2) inhibiting or arresting the development of the disease; or (3) regressing or reversing the disease state.

In the case of gastrointestinal inflammation, particularly that occurring in mammals, the present invention inhibits gastrointestinal inflammatory disease from a number of causes. For example, Oncostatin M is shown in in vivo models described herein to be effective against drug-induced gastrointestinal inflammatory disease. The drug employed in the Examples described herein, dextran sodium sulfate (DSS), induces both acute and chronic gastrointestinal inflammation. Purified Oncostatin M is efficacious in reducing both the severity of injury and the degree of inflammation. The composition of the invention can be administered, therefore, in cases of gastric colitis or the like, wherein symptoms include, but are not limited to, acute cytotoxicity of colonic epithelial cells and corresponding inflammatory-induced tissue damage. Oncostatin M can be used in methods and compositions for reducing the severity of ulcerative colitis, a disease which primarily affects the distal colon and which is characterized by broad-based ulcers and accompanying glandular loss and fibrous tissue replacement. Oncostatin M also alleviates the peritonitis resulting from inflammatory cell infiltration. Additionally, Oncostatin M treatment reduces the injury and inflammation in gastric colitis by limiting the severity of crypt loss, mucosal atrophy, erosions, and broad-based ulcers. According to the present invention Oncostatin M is useful for treating a variety of inflammatory bowel diseases, such as Crohn's Disease, ulcerative colitis, and irritable bowel syndrome.

In another embodiment Oncostatin M is used in methods for treating rheumatoid arthritis. Rheumatoid arthritis is a chronic inflammatory disease primarily of the joints that may result in permanent loss of joint function. Irreversible loss of joint function is attributed to severe degradation of collagen and degradation of bone, ligament and tendon. The chronic inflammatory disease associated with rheumatoid arthritis, and thus the manifestations of the disease, are treated by administering Oncostatin M in amounts sufficient to inhibit inflammation at one or more sites of existing or potential joint inflammation. Administration can take a variety of routes but will be parenterally or orally, more typically by intramuscular, intravenous, or subcutaneous injection or injection at or near joints targeted for treatment, e.g., into synovial fluid or the like.

In another embodiment Oncostatin M is used in methods for treating multiple sclerosis. Multiple sclerosis is a chronic central nervous system disease characterized by immune-mediated demyelination of the white matter of the brain and spinal cord. Infiltrates of T cells (both helper and cytotoxic) and macrophages are observed at the sites of demyelination. Chronic and acute episodes associated with multiple sclerosis are treated by administering Oncostatin M in amounts sufficient to inhibit inflammatory immune response at one or more sites of existing or potential demyelination in the brain. Oncostatin M is used in methods for treating experimental allergic encephalomyelitis (EAE). Like multiple sclerosis, EAE is an inflammatory disease of the central nervous system. EAE is inducible in a variety of mammals by injecting brain or spinal cord tissue with an adjuvant. Within the brain perivascular infiltration of inflammatory cells precedes clinical symptoms. EAE is regarded as a model of other CNS inflammatory diseases, particularly multiple sclerosis and human autoimmune thyroiditis. Administration of Oncostatin M to treat multiple sclerosis or other diseases which EAE models can take a variety of routes, e.g., orally or parenterally, more typically by intramuscular, intravenous, or subcutaneous injection, or infusion into cerebrospinal fluid or ventricles at or near afflicted areas. In this use, the precise amounts, frequency, and duration of treatment will depend on the status of the disease and the patient's state of health and weight, the mode of administration, the nature of the formulation, etc. These factors will vary such that specific regimens can be established to maximize efficacy of treatment.

Compositions useful in the methods described herein are those which comprise Oncostatin M or a biologically active fragment, mutant, analog or fusion construct thereof. In the practice of this invention, use of the term "Oncostatin M" is intended to refer also to the biologically active variants. Methods for the production of Oncostatin M are provided in U.S. Pat. Nos. 5,428,012 and 5,451,506 to Shoyab et al., which are incorporated herein by reference. The mature (circulating) form of Oncostatin M contains about 196 ($Ala^1$-$Arg^{196}$) amino acid residues. Oncostatin M is produced originally as a pre-propolypeptide containing a signal peptide of approximately 25 amino acids. After signal peptide cleavage there remains a polypeptide of approximately 227 residues ($Ala^1$-$Arg^{227}$), which is further processed by proteolytic cleavage to yield the final circulating polypeptide, $Ala^1$-$Arg^{196}$ (or also $Ala^1$-$Arg^{195}$). Additionally, further cleavage of residues from the C-terminal domain of Oncostatin M (for example, down to $Ala^1$-$Ser^{185}$) has been demonstrated not to prevent the biological activity of Oncostatin M. See, e.g., Int'l Publication PCT WO91/09057 (U.S. Ser. No. 623,867), incorporated herein by reference.

cDNA and genomic cloning of Oncostatin M, the amino acid and DNA sequence thereof, and also the expression of functional Oncostatin M polypeptide from recombinant mammalian cells have been described in Malik et al., *Mol. Cell. Biol.* 9:2847–2853 (1989). Considerable information is available concerning the structural organization of the Oncostatin M polypeptide and of the identity of the subregions thereof needed for functional activity. See, e.g., Kallestad et al., *J. Biol. Chem.* 264:4282–4289 (1989), incorporated herein by reference. Therapeutic compositions useful in the practice of the present invention comprise Oncostatin M or one or more biologically active fragments, mutants, analogs or fusion constructs thereof. For the purposes of the present invention all such biologically active molecules are included in the meaning of the term "Oncostatin M" as used herein. Such molecules are considered "biologically active" if they demonstrate growth inhibition of certain neoplastic cell lines (A375), induction of IL-6 from endothelial cells, induction of TIMP-1 from fibroblasts, or a specific binding affinity for a cellular receptor for Oncostatin M, and the ability to inhibit the inflammatory response in a mammalian host or in a suitable in vitro assay. Various genetic modifications of recombinant Oncostatin M can be used to encode biologically active Oncostatin M molecules effective in the treatment regimens described herein.

Methods for producing Oncostatin M by recombinant DNA techniques are described in U.S. Pat. Nos. 5,428,012 and 5,451,506. Suitable hosts for expressing Oncostatin M include both eukaryotic and prokaryotic cells. Among suitable eukaryotic cells are mammalian cells, including CHO cells, insect cells, and yeast cells. Suitable expression vectors will generally comprise a promoter capable of directing the transcription of an Oncostatin M polynucleotide molecule of interest in a host cell. Representative expression vectors may include both plasmid and/or viral vector sequences. Suitable vectors include retroviral vectors, vaccinia viral vectors, CMV viral vectors, BLUESCRIPT, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomegalovirus promoter (Boshart et al., *Cell* 41: 521–530 (1985)) and the SV40 promoter (Subramani et al., *Mol. Cell. Biol.* 1: 854–864 (1981)). Suitable cellular promoters for expression of proteins in mammalian host cells include but are not limited to the mouse metallothionien-1 promoter (Palmiter et al., U.S. Pat. No. 4,579,821), and tetracycline-responsive promoter (Gossen and Bujard, *Proc. Natl. Acad. Sci. U.S.A.* 89: 5547–5551 (1992), and Pescini et al., *Biochem. Biophys. Res. Comm.* 202:1664–1667 (1994)). Also contained in the expression vectors is a transcription termination signal located downstream of the coding sequence of interest. Suitable transcription termination signals include the early or late polyadenylation signals from SV40 (Kaufman and Sharp, *Mol. Cell. Biol.* 2:1304–1319 (1982)), the polyadenylation signal from the Adenovirus 5 e1B region and the human growth hormone gene terminator (DeNoto et al., *Nucleic Acid. Res.* 9: 3719–3730 (1981)).

Mammalian cells may be transfected by a number of methods including calcium phosphate precipitation (Wigler et al., *Cell* 14: 725 (1978), Corsaro and Pearson, *Somatic Cell Genetics* 7: 603 (1981), Graham and Van der Eb, *Virology* 52: 456 (1973)); lipofection (Felgner et al., *Proc. Natl. Acad. Sci. U.S.A.* 84: 7413–7417 (1987)), microinjection and electroporation (Neumann et al., *EMBO J.* 1: 841–845 (1982)). Mammalian cells can be transduced with virus such as SV40, CMV and the like. In the case of viral vectors, cloned DNA molecules may be introduced by infection of susceptible cells with viral particles.

As would be evident to one of ordinary skill in the art, the polynucleotide molecules of the present invention may be expressed in *Saccharomyces cerevisiae,* methylotrophic yeast (e.g., *Pichia pastoris*), filamentous fungi, *E. coli,* and a variety of other cellular hosts. Methods for expressing cloned genes in *Saccharomyces cerevisiae* are generally known in the art (see, "Gene Expression Technology," *Methods in Enzymology,* Vol. 185, Goeddel (ed.), Academic Press, San Diego, Calif., 1990 and "Guide to Yeast Genetics and Molecular Biology," *Methods in Enzymology,* Guthrie and Fink (eds.), Academic Press, San Diego, Calif., 1991; which are incorporated herein by reference). Methods for expressing genes and cDNAs in cultured mammalian cells and in *E. coli* is discussed in detail in Sambrook et al. (*Molecular Cloning, A Laboratory Manual,* Second Ed., Cold Spring Harbor, N.Y., 1989; which is incorporated herein by reference).

The methylotrophic yeast grow rapidly to high biomass on minimal defined media, and gene expression can be driven by a strong, tightly regulated promoter. There are a number of methanol responsive genes in methylotrophic yeast, the expression of each being controlled by methanol responsive promoters, which promoters can be used to control the expression of Oncostatin M. Most commonly, expression of Oncostatin M in methylotrophic yeast is driven by a promoter of an alcohol oxidase structural gene, such as the AOX1 gene of *P. pastoris,* the AOX2 gene of *P.*

*pastoris* (U.S. Pat. Nos. 4,855,231, 5,032,516 and 5,166,329, incorporated herein by reference), the MOX1 gene of *Hansenula polymorpha* or *Candida biodinii* (U.S. Pat. No. 5,389,525, incorporated herein by reference), or the like. The expression level of the AOX1 mRNA is tightly regulated with respect to carbon source, and the AOX1 promoter is a strong, tightly regulated promoter for the expression of Oncostatin M. The sequences of alcohol oxidase genes of other methylotrophic yeast are known, e.g., Cregg et al., *Mol. Cell. Biol.* 9:1316–1323 (1989); Ellis et al., *Mol. Cell. Biol.* 5: 1111–1121 (1985); and Ledeboer et al., *Nucleic Acids Res.* 13: 3063–3082 (1985), each of which is incorporated herein by reference, and these genes share distinct regions of identity.

Expression vectors for use in methylotrophic yeast comprise a methanol responsive promoter, such as the AOXI promoter, or other methanol inducible promoter operatively linked to and capable of directing the transcription of the cloned Oncostatin M DNA, and a transcriptional terminator operatively linked to the Oncostatin M DNA. (The term "operatively linked" indicates that the segments are arranged so that they function in concert for their intended purposes, e.g., transcription initiates in the promoter and proceeds through the coding segment to the terminator; see Sambrook et al., supra.) The expression vectors may contain additional elements, such as an origin of replication, one or more selectable markers allowing amplification in alternative hosts, unique restriction sites into which an Oncostatin M encoding gene is inserted such as, e.g., EcoRI, etc. Expression vectors suitable for insertion and expression of the Oncostatin M polynucleotide sequences are also available from commercial suppliers, such as a Pichia Expression Kit supplied by Invitrogen, San Diego, Calif.

In one embodiment, a recombinant human Oncostatin M derivative is expressed in the yeast *Pichia pastoris*. *Pichia pastoris* expressed recombinant human Oncostatin M derivatives (PiOM) are under the transcriptional regulation of a strong inducible promoter such as AOX-1. Fusion of the human Oncostatin M cDNA derivatives in-frame to the α-mating factor or other leader sequence facilitates efficient secretion of Oncostatin M into the culture supernatant. *Pichia pastoris* offers the advantages of post-translational modification, including proteolytic processing, protein refolding, and carbohydrate addition. *Pichia pastoris* can be cultured to high cell density by fermentation and the PiOM derivatives can be rapidly and efficiently isolated from the culture supernatant, e.g., using a simple two-step chromatography protocol, which yields protein of pharmaceutical quality and which is efficacious in the methods of the present invention.

One exemplary yeast expressed Oncostatin M derivative described herein comprises a human cDNA fragment, which encodes the mature form of Oncostatin M less 33 carboxy-terminal amino acids, fused in-frame to the α-mating factor leader sequence and downstream of the AOX-1 methanol inducible promoter. Another Oncostatin M derivative comprises three mutations in the human cDNA coding region such that amino acid 77 is glycine, amino acid 152 is alanine, and amino acid 154 is alanine (PiOM-194[TKO]).

For use in the present invention Oncostatin M will be formulated as a pharmaceutically active molecule in a physiologically acceptable carrier to permit its administration to mammals, including humans. The Oncostatin M is administered in one or more doses so as to effectively treat the disorders described herein. An appropriate dose will typically be in the range of about 0.5 μg to 1 mg Oncostatin M/kg body mass, more typically from about 1 μg to about 100 μg/kg body mass. Single or multiple administrations of the compositions can be carried out with dose levels and pattern being selected by the health professional. In this use, the precise amounts, frequency, and duration will depend on the patient's state of health and weight; the mode of administration; the nature of the formulation; etc. These factors will vary in specific regimens such that they maximize the efficacy of the treatment. It must be kept in mind that the methods of the present invention may generally be employed in serious disease or injury states, that is, life-threatening or potentially life threatening situations. In such cases, in view of the minimization of extraneous substances and general lack of immunogenicity of Oncostatin M, it is possible and may be felt desirable to administer substantial excesses of these compositions. The Oncostatin M may be variously administered, orally or parenterally as preferred for the specific disease to be treated, and the effective dose may well vary depending on the route of administration. It is further anticipated that Oncostatin M may be administered in combination with other agents efficacious against inflammatory diseases or the specific indications described herein.

The pharmaceutical compositions of oncostatin M for parenteral or oral administration typically comprise a solution of the Oncostatin M molecule dissolved in an acceptable carrier, preferably an aqueous carrier. A variety of aqueous carriers may be used, e.g., water, buffered water, 0.4% saline, 0.3% glycine and the like. The Oncostatin M molecules can also be formulated into liposome preparations for delivery or targeting to sites of injury. Liposome preparations are generally described in, e.g., U.S. Pat. No. 4,837,028, U.S. Pat. No. 4,501,728, and U.S. Pat. No. 4,975,282, incorporated herein by reference. The compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. The concentration of Oncostatin M in these formulations can vary widely, i.e., from less than about 0.5%, usually at or at least about 1% to as much as 15 or 20% by weight and will be selected primarily by fluid volumes, viscosities, etc., in accordance with the particular mode of administration selected.

Given the numerous causes of gastrointestinal inflammation including microbial infections, burns, radiation, and chemical agents such as toxins and caustic substances, this invention provides a wide range of applications for Oncostatin M. While gastrointestinal inflammatory diseases, rheumatoid arthritis, multiple sclerosis and other EAE-like disorders are described herein in as a specific application of Oncostatin M, this is not intended to limit the wide scope of potential therapeutic uses for treatment of related inflammatory diseases. For example, Oncostatin M may also be efficacious in the treatment of other disease states including, but not limited to: allergic rhinitis; allergic bronchial asthma; chronic obstructive pulmonary disease; emphysema; acute respiratory distress syndrome; immediate hypersensitivity reactions, such as allergic conjunctivitis; osteoarthritis, tendinitis, bursitis, psoriasis, dermatitis, eczema, seborrhea; and uveitis, among others.

Human Oncostatin M or derivatives, constructed and isolated as described in this application, can be tested in vivo in murine or non-human primate (e.g. cynmolgus and Rhesus monkey) models to test, e.g., their efficacy against different forms of gastrointestinal inflammation, inhibition of LPS induced TNF-α production, synergy with TNF-α in IL-6 production, stimulation of acute phase protein expression, or the like. Procedures for these in vivo tests are included herein for reference.

The following examples are provided by way of illustration, not limitation.

EXAMPLE I

Oncostatin M for Treating Gastrointestinal Inflammation

This Example describes the efficacy of oncostatin M in an in vivo model system of acute and chronic gastrointestinal inflammation.

Oncostatin M was produced and purified from the CHO cell line pSV2βOM, which is described in U.S. Pat. No. 5,428,012. This cell line was generated by constructing an expression plasmid which included a fusion of the TGF-β signal peptide sequence to the pro-Oncostatin M cDNA, encoding a 227 amino acid form of Oncostatin M (CHO-OM), as described in U.S. Pat. No. 5,428,012. This expression plasmid was transfected into dhfr(−) CHO cells that underwent stepwise amplification with methotrexate.

Hollow-fiber technology (Cell Pharm, Unisyn Technologies) was used to generate conditioned medium from the CHO-OM cell line. Serum-free media (DME:F12, Hyclone and EX-CELL 301, JRH Biosciences) were used in four production runs. With DME:F12 medium, the culture ran 13 days. With EX-CELL 301 medium, cultures were maintained for 29 days, 67 days and 50 days. Each hollow-fiber system was seeded with cells from roller bottles that contained 1% fetal bovine serum. Titers approximated 11 to 14 µg/ml Oncostatin M protein in low serum or serum-free medium. In addition to Oncostatin M protein, the conditioned medium from CHO cells contained significant levels of endogenous contaminating proteins. Therefore, four chromatography steps were employed to yield a highly homogeneous (>95%) preparation of Oncostatin M. The chromatography steps generally employed were: Q-Sepharose, S-Sepharose, hydroxyapatite, and preparative C4 reversed-phase HPLC. The final purification step ensured separation of Oncostatin M from a major contaminating protein that was identified as TIMP-1 (hamster) by sequence analysis, which was probably induced in the CHO cells in response to Oncostatin M.

CHO-derived Oncostatin M migrated with an apparent molecular mass of 28.5 kDa by SDS-PAGE. In vitro, Oncostatin M has an $IC_{50}$ that ranges between 0.1 and 10 ng/ml in the A375 growth inhibitory assay, reflecting the combination of both assay and batch to batch variation.

In the animal studies, groups of five Swiss-Webster mice were given 5% dextran sodium sulfate (DSS) or nothing ("None") in their drinking water; DSS induces both acute and chronic colitis. One group of animals receiving DSS received no other treatment ("None"). Other DSS groups received either Oncostatin M (15 µg) or control solutions (PBS) twice daily for 10 days. Animals were sacrificed on day 13. The entire colon was opened longitudinally to evaluate any gross morphologic changes, then immersion-fixed in 10% neutral buffered formalin. The colon was divided into two equal segments, proximal and distal. Each segment was serially stepped sectioned. The tissues were embedded in paraffin by routine methods, sectioned at 6 µm, stained with hematoxylin and eosin (H&E), and examined by light microscopy. The sections were graded without knowledge of treatment as to the severity of crypt injury and degree of inflammation. The crypt injury was scored as follows: grade 0, intact crypt; grade 1, loss of the basilar one-third of the crypt; grade 2, loss of the basilar two-thirds of the crypt; grade 3, loss of the entire crypt with the surface epithelium remaining intact; grade 4, loss of both the entire crypt and surface epithelium resulting in an erosion. These changes were quantitated as to the percentage of tissue involvement by the disease process: (1) 0–25%; (2) 26–50%; (3) 51–75%; and (4) 76–100%. Each piece of tissue was scored with a grade and percentage area involvement with the product of the two being the severity of injury. The scoring for severity of inflammation was as follows: grade 0, nonremarkable; grade 1, minimal; grade 2, mild; grade 3, moderate; and grade 4, severe. The extent of involvement was estimated at: (1) 0–25%; (2) 26–50%; (3) 51–75%; and (4) 76–100%. The inflammatory score was the product of severity grading multiplied by extent of involvement. The scoring process was performed on each section of colon. Scores were summed and divided by the number of pieces of tissue for each segment, similar to that obtained for injury scores. Data was expressed as the mean and standard error of the mean. Statistical analysis was performed using multivariate analysis of variance (MANOVA) followed by Dunnett's multiple comparisons. Significance was accepted at the $p<0.05$ level.

Mechanistic studies in the DSS murine model suggest that the initial acute injury is the result of a direct cytotoxic effect on the colonic epithelial cells in the first three to five days following initiation of DSS. In response to this injury, an inflammatory response occurs which leads to a second phase of tissue damage. As shown in Table 1, the colons of animals that received untreated drinking water with no concurrent treatment ("None-None") had little injury or inflammation. In contrast, groups given DSS but no treatment ("DSS-None" or "DSS-PBS") had significantly higher cumulative scores for injury and inflammation. The scores of the Oncostatin M-treated animals were significantly improved compared to the DSS-None and DSS-PBS groups.

The predominant histopathologic changes in DSS-treated control mice were characterized as broad-based ulcers accompanied by a severe glandular loss and fibrous connective tissue replacement. A prominent inflammatory cell infiltrate occasionally extended through the muscular layers with resulting peritonitis. There was a sharp demarcation between diseased and unaffected bowel segments. In a representative light photomicrograph of the colon from an animal treated with DSS-PBS and sacrificed at day 12 there was a large ulcer following a severe transmural injury that extended through the muscular layers and resulted in a diffuse peritonitis. The ulcerated area was characterized by severe glandular loss with fibrous connective tissue replacement and a chronic active inflammatory cell infiltrate. The DSS-induced changes observed are similar to those reported in an extensive histopathological time-course study in mice given oral DSS (Cooper et al., (1993)). Several of the changes observed in the DSS-treated mice in this study were also similar to those observed in ulcerative colitis, including a disease process that most severely affected the distal colon and extended in a retrograde fashion, with broad-based ulcers, and a superficial inflammatory response that usually affected only the mucosa and submucosa.

Oncostatin M was effective in reducing both the severity of injury and degree of inflammation as the cumulative scoring was significantly less in the DSS-Oncostatin M groups as compared to animals receiving DSS and no concurrent treatment (p<0.05). The morphologic injury and inflammation in Oncostatin M-treated mice were similar to changes observed in animals receiving DSS and no concurrent treatment, but the level of severity was markedly reduced. Thus, a representative light photomicrograph of the colon from an animal treated with DSS-Oncostatin M and sacrificed at day 12 showed a small healed ulcer, and the ulcerated area was characterized by focal glandular loss with fibrous connective tissue replacement and a reepithelialized surface. The inflammatory cell infiltrate was minimal.

TABLE 1

Inhibition of Gastrointestinal Injury by Oncostatin M

| Treatment (N = 5) | Injury | | Inflammation | |
|---|---|---|---|---|
| None-None | 0.31 ± 0.07 | | 0.17 ± 0.06 | |
| DSS-None | 4.67 ± 0.90 | *p < 0.01 | 3.60 ± 0.51 | *p < 0.01 |
| DSS-PBS | 4.10 ± 0.83 | *p < 0.01 | 2.94 ± 0.59 | *p < 0.02 |
| DSS-OM | 1.39 ± 0.39 | #p < 0.03 | 1.33 ± 0.52 | #p < 0.05 |

Data presented as the mean and standard error.
* = p value as compared to the None-None group.
# = p value as compared to the DSS-None group.

In a second study, Oncostatin M was able to inhibit both the injury and inflammation associated with DSS-treatment in a dose-dependent manner. DSS-animals treated with Oncostatin M at 30 μg daily for 10 days showed no statistically significant difference from control animals that did not receive DSS (Table 2). At 3 μg and 0.3 μg of Oncostatin M (daily for 10 days) there were increases in cumulative scores for the severity of tissue injury and degree of inflammation compared to normal controls (no DSS). However, both Oncostatin M doses reduced the severity of DSS induced injury and inflammation (p<0.05). One group of animals received three days of DSS water prior to the initiation of Oncostatin M treatment. By then, significant injury and inflammation had already occurred.

TABLE 2

DSS-induced Colitis: Cumulative Scoring

| Treatment (N = 5) | Injury | Inflammation |
|---|---|---|
| Day 3 | | |
| DSS-None | 3.56 ± 0.65 | 1.37 ± 0.45 |
| DSS-OM 30 μg | 2.61 ± 0.40 ++ | 0.99 ± 0.35 ++ |
| Day 10 | | |
| None-None | 0.23 ± 0.07 ++ | 0.18 ± 0.05 ++ |
| DSS-None | 9.55 + 0.97 ** | 4.45 ± 0.52 ** |
| DSS-OM 0.3 μg | 4.70 ± 0.87 **, + | 2.88 ± 0.48 **, + |
| DSS-OM 3 μg | 4.03 ± 0.89 **, ++ | 2.78 ± 0.54 **, + |
| DSS-OM 30 μg | 3.32 ± 1.15 *, ++ | 1.87 ± 0.59 *, ++ |
| DSS-OM D3[a] 30 μg | 5.52 ± 1.06 ** | 2.33 ± 0.41 **, + |
| None-OM 30 μg | 0.17 ± 0.05 ++ | 0.19 ± 0.06 ++ |

Animals were treated as above with the indicated doses of Oncostatin M intravenously.
Data presented as the mean score ± S.D.
** = p < 0.01; * = p < 0.05 as compared to the None-None group.
++ = p < 0.01; + = p < 0.05 as compared to the DSS-None group.
[a] = treatment with Oncostatin M delayed until Day 3.

Animals receiving Oncostatin M had a reduction in inflammation even in the presence of injury (p<0.05) indicating that Oncostatin M is capable of reducing already initiated inflammation and injury.

In a third efficacy study, animals were sacrificed at three or seven days following DSS treatment. Groups of five mice were give 5% DSS in their drinking water. One day following initiation of DSS treatment animals were treated with Oncostatin M (10 μg/day,i.p), or control diluent. Animals were sacrificed on day 13. The entire colon was opened longitudinally to evaluate any gross morphologic changes, then immersion fixed in 10% neutral buffered formalin. The colon was divided into three equal segments, proximal, middle and distal. Each segment was serially-stepped sectioned. The tissues were embedded in paraffin by routine methods, sectioned at 6 μm, stained with hematoxylin and eosin (H&E), and examined by light microscopy. The sections were graded without knowledge of treatment as to the severity of crypt injury and degree of inflammation. The crypt injury was scored as follows: grade 0, intact crypt; grade 1, loss of the basilar one-third of the crypt; grade 2, loss of the basilar two-thirds of the crypt; grade 3, loss of the entire crypt with the surface epithelium remaining intact; grade 4, loss of both the entire crypt and surface epithelium resulting in an erosion. These changes were quantitated as to the percentage of tissue involvement by the disease process: (1) 0–25%; (2) 26–50%; (3) 51–75%; and (4) 76–100%. The inflammatory score was the product of severity grading multiplied by extent of involvement. The scoring process was performed on each section of colon. Scores were summed and divided by the number of pieces of tissue for each segment, similar to that obtained for injury scores. Data was expressed as the mean and standard error of the mean. Statistical analysis was performed using multivariate analysis of variance (MANOVA) followed by Dunnett's multiple comparisons. Significance was accepted at the p<0.05 level. Data are presented as the mean and standard error.

Histopathological changes observed in this study increased in severity from the day three to the day seven time point (see Table 3). At day three, colonic lesions were minimal to mild in severity; animals treated with Oncostatin M had a trend toward improvement compared to the day three DSS-positive controls. However, the extent of the injury was limited at this time and the differences were not significant. By day seven, however, the nature of the colonic lesions in DSS animals were similar to those described in earlier DSS-induced colitis mouse studies consisting of crypt loss, mucosal atrophy, erosions, and broad-based ulcers. Statistically significant differences in cumulative injury and inflammatory scores were present in the Oncostatin M-treated animals at the day seven time point as compared to the respective DSS controls. Results from this study indicate that DSS-induced colonic lesions become progressively more severe from days three to seven. At the day seven time point, a significant decrease in both injury and inflammatory scores were observed in the Oncostatin M-treated animals.

TABLE 3

| Treatment | Day | Proximal | Middle | Distal | Cumulative |
|---|---|---|---|---|---|
| Mean Regional and Cumulative Injury Scores Over Time | | | | | |
| DSS Control | 3 | 2.17 ± 0.44 | 1.08 ± 0.17 | 2.08 ± 0.60 | 1.78 ± 0.28 |
| OM | 3 | 1.08 ± 0.22 | 0.5 ± 0.22 | 1.33 ± 0.22 | 1.00 ± 0.16 |
| DSS Control | 7 | 6.50 ± 1.80 | 7.42 ± 1.34 | 6.83 ± 1.36 | 6.92 ± 0.77 |
| OM | 7 | 1.00 ± 0.14 | 1.17 ± 0.08[a] | 1.58 ± 0.17[a] | 1.25 ± 0.11[b] |
| Mean Regional and Cumulative Inflammatory Scores Over Time | | | | | |
| DSS Control | 3 | 1.42 ± 0.22 | 0.33 ± 0.08 | 0.83 ± 0.30 | 0.86 ± 0.19 |

TABLE 3-continued

| Treatment | Day | Proximal | Middle | Distal | Cumulative |
|---|---|---|---|---|---|
| OM | 3 | 0.67 ± 0.44 | 0.42 ± 0.17 | 0.92 ± 0.33 | 0.67 ± 0.18 |
| DSS Control | 7 | 7.75 ± 0.66 | 7.17 ± 0.88 | 4.75 ± 0.52 | 6.56 ± 0.58 |
| OM | 7 | 0.67 ± 0.42[a] | 1.58 ± 0.87 | 1.25 ± 0.58[a] | 1.17 ± 0.35[b] |

[a]Statistically different from respective DSS Control group ($p < 0.05$).
[b]Statistically different from respective DSS Control group ($p < 0.001$).

EXAMPLE II

Efficacy of Orally Administered Oncostatin M for Colitis

This Example describes the inhibition by Oncostatin M of colitis in a murine model when Oncostatin M is administered orally. The treatment of gastrointestinal injury allows a potential local delivery of the protein by oral administration. This local delivery could be advantageous in reducing systemic toxicity, improving efficacy and easing chronic administration. The stability of Oncostatin M to acid exposure and proteolytic degradation further supports the suitability of this route of administration. Epithelial cells, including those of the gut lining (Cichy et al. 1995b), and vascular endothelial cells (Brown et al. 1991), are known to have receptors for this protein.

Colitis was induced as described in Example I by administration of 5% DSS water for 7 days. One day following DSS, animals were treated by oral administration of Oncostatin M (100 μg/day) or control diluent (PBS) (100 μg/day), by gavage for days 1–11. A 200 μl volume of protein or diluent was administered using a 24 gauge feeding needle. Control animals had gastrointestinal injury and inflammation consistent with other studies with damage increasing from proximal to distal regions of the colon (Table 4). Animals receiving oral Oncostatin M had a statistically significant reduction of both the inflammation and injury compared to control ($p<0.05$). These results support oral-based therapy for Oncostatin M in this indication.

TABLE 4

| DSS | Treatment | Proximal | Middle | Distal | Cumulative |
|---|---|---|---|---|---|
| no | none | 0.38 ± 0.24 | 0.56 ± 0.16 | 0.81 ± 0.06 | 0.58 ± 1.10[a] |
| yes | PBS | 3.31 ± 0.66 | 5.62 ± 3.19 | 6.37 ± 3.21 | 5.10 ± 1.43 |
| yes | OM | 1.80 ± 0.54 | 1.20 ± 0.39 | 1.35 ± 0.61 | 1.45 ± 0.28[a] |
| | Mean Regional and Cumulative Inflammatory Scores | | | | |
| no | none | 0.25 ± 0.25 | 0.00 ± 0.00[a] | 0.00 ± 0.00 | 0.08 ± 0.08[a] |
| yes | PBS | 4.75 ± 1.42 | 5.50 ± 2.32 | 4.31 ± 1.91 | 4.85 ± 1.01 |
| yes | OM | 2.35 ± 0.85 | 2.00 ± 0.89 | 0.75 ± 0.34 | 1.70 ± 0.43[a] |

Data presented as the mean score ± S.D.
[a] = Statistically different from PBS control mice (MANOVA; $p < 0.05$)

EXAMPLE III

Comparison of Oncostatin M. Prednisone and Sulfadiazine for IBD

This Example compares the in vivo effects of Oncostatin M to prednisone and sulfasalazine, two current therapies used for treating inflammatory bowel disease (IBD). Colitis was induced by DSS as described above. Parentally administered Oncostatin M (10 or 30 μg, i.p., days 1–10) was significantly ($p<0.02$) effective in ameliorating DSS-induced injury and inflammation as compared to DSS-positive controls. Prednisone or sulfasalazine administered on the same schedule were not active in reducing DSS-induced colitis. These studies clearly delineate differences in the biological consequences of treatment with Oncostatin M and other existing drugs in this disease.

TABLE 5

| Treatment | Proximal | Middle | Distal | Cumulative |
|---|---|---|---|---|
| Mean Regional and Cumulative Injury Scores | | | | |
| Oncostatin: 10 μg (ip) | 1.00 ± 0.44 | 0.72 ± 0.29[a] | 0.97 ± 0.45 | 0.89 ± 0.22[a] |
| Oncostatin: 30 μg (ip) | 1.19 ± 0.45 | 2.99 ± 1.03 | 2.26 ± 0.93 | 2.15 ± 0.49[a] |
| Pred 3.0 mg/kg (im) | 6.49 ± 3.17 | 10.74 ± 2.30 | 11.66 ± 1.37 | 9.63 ± 1.42 |
| Pred 1.5 mg/kg (im) | 7.79 ± 2.29 | 10.73 ± 2.4 | 11.60 ± 2.22 | 10.04 ± 1.32 |
| Sulpha 300 mg/kg (po) | 7.99 ± 1.53 | 9.27 ± 2.60 | 11.44 ± 1.58 | 9.57 ± 1.12 |
| Sulpha 100 mg/kg (po) | 3.66 ± 0.31 | 6.26 ± 2.01 | 6.79 ± 2.51 | 5.57 ± 1.06 |
| Control | 4.50 ± 0.74 | 8.70 ± 1.38 | 7.73 ± 1.20 | 6.98 ± 0.69 |
| Mean Regional and Cumulative Inflammatory Scores | | | | |
| Oncostatin: 10 μg (ip) | 0.88 ± 0.46[a] | 1.38 ± 0.41 | 2.38 ± 0.51 | 1.55 ± 0.29[a] |
| Oncostatin: 30 μg (ip) | 1.59 ± 0.69[a] | 3.26 ± 0.94 | 2.72 ± 0.83 | 2.52 ± 0.48[a] |
| Pred 3.0 mg/kg (im) | 5.41 ± 1.46 | 6.58 ± 0.34 | 6.99 ± 0.63 | 6.33 ± 0.53 |
| Pred 1.5 mg/kg (im) | 5.72 ± 1.76 | 7.12 ± 1.29 | 4.40 ± 0.81 | 5.75 ± 0.77 |
| Sulpha 300 mg/kg (po) | 5.55 ± 0.84 | 4.55 ± 1.18 | 3.94 ± 0.26 | 4.68 ± 0.48 |
| Sulpha 100 mg/kg (po) | 6.06 ± 1.22 | 7.06 ± 0.92 | 5.93 ± 1.18 | 6.35 ± 0.61 |
| Control | 5.59 ± 0.66 | 6.53 ± 0.86 | 4.35 ± 0.59 | 5.49 ± 0.42 |

[a]Statistically different from control (MANOVA, $p < 0.02$)

EXAMPLE IV

Oncostatin M Inhibits LPS-Induced TNF-α Production

This Example describes the inhibition by Oncostatin M of LPS induced TNF-α production and the synergistic effect of co-administering Oncostatin M with LPS or TNF-α on IL-6 levels in vivo.

Figure 1A:
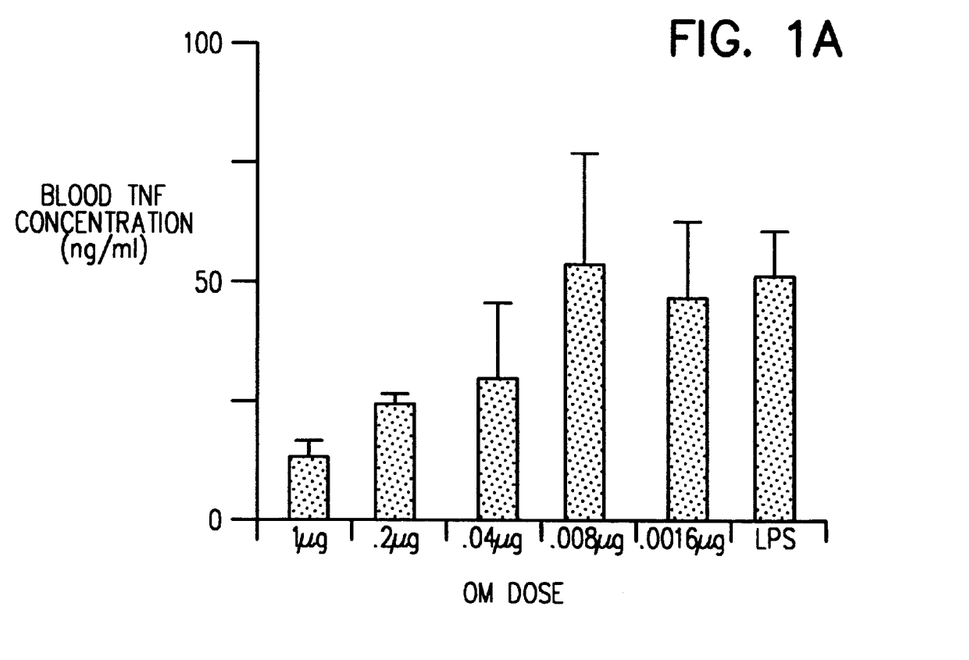
FIG. 1A and 1B collectively show LPS induced TNF-α regulation by oncostatin M.
Figure 1B:
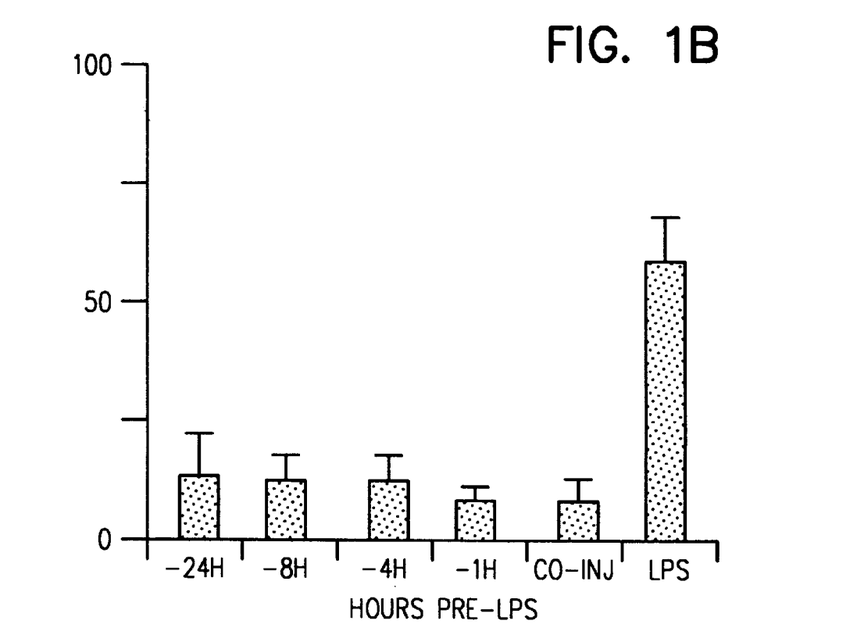

The effects of Oncostatin M on TNF-α production were studied. Groups of three C57/BL6 mice were injected with various doses of Oncostatin M (FIG. 1A) or at the described time points prior to LPS (FIG. 1B) in combination with 1 microgram LPS intravenously. Blood was sampled at various time points, plasma removed and assayed for TNF-α by ELISA. As shown in FIG. 1A, at one hour, Oncostatin M inhibited the induction of TNF-α by LPS. It was active over a large dose range (0.1 μg to 10 μg per mouse). It was not necessary to administer Oncostatin M concurrently with the LPS, since it could be administered 24 hours prior to LPS and still be effective (FIG. 1B). The short half-life of Oncostatin M (minutes) thus suggests that its effects may be partially indirect.

It was next established that the effects of Oncostatin M on inflammatory cytokines were more general, and not limited to changes in TNF-α levels. Since IL-6 is well established to be important in inflammation, and is regulated in vivo by both Oncostatin M and TNF-α, the IL-6 levels in mice receiving a combination of LPS and Oncostatin M were measured. The combination of LPS and Oncostatin M produced levels of IL-6 significantly greater that the IL-6 levels produced by LPS or Oncostatin M alone. This was a particularly surprising result, as LPS-induced IL-6 is a result of TNF-α production and Oncostatin M blocks TNF-α. Therefore, Oncostatin M is able to inhibit proinflammatory cytokines while augmenting the normal feedback of anti-inflammatory cytokines.

Figure 2A:
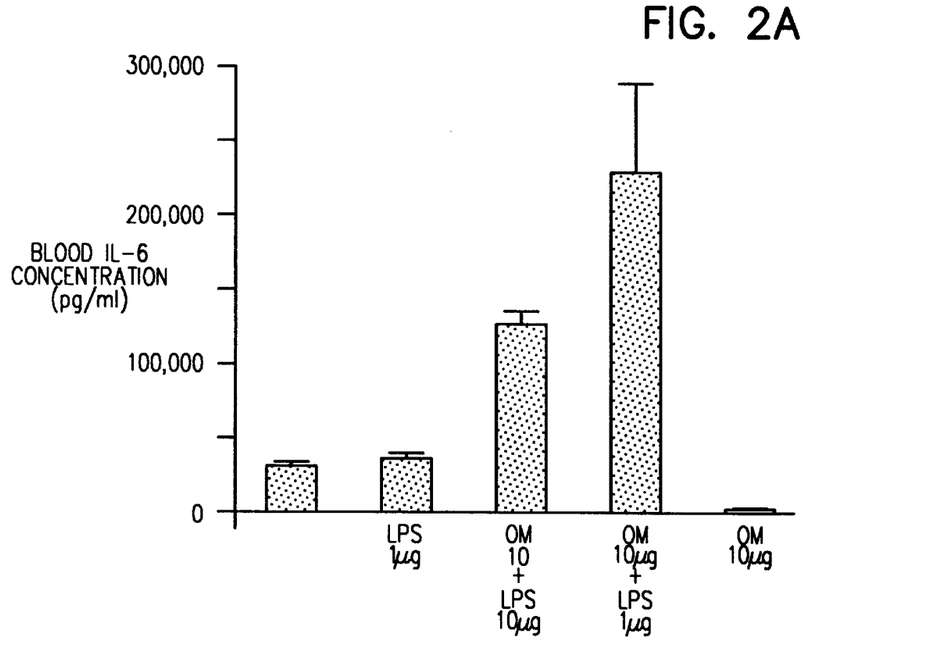
FIG. 2A and 2B collectively show IL-6 upregulation by Oncostatin M.
Figure 2B:
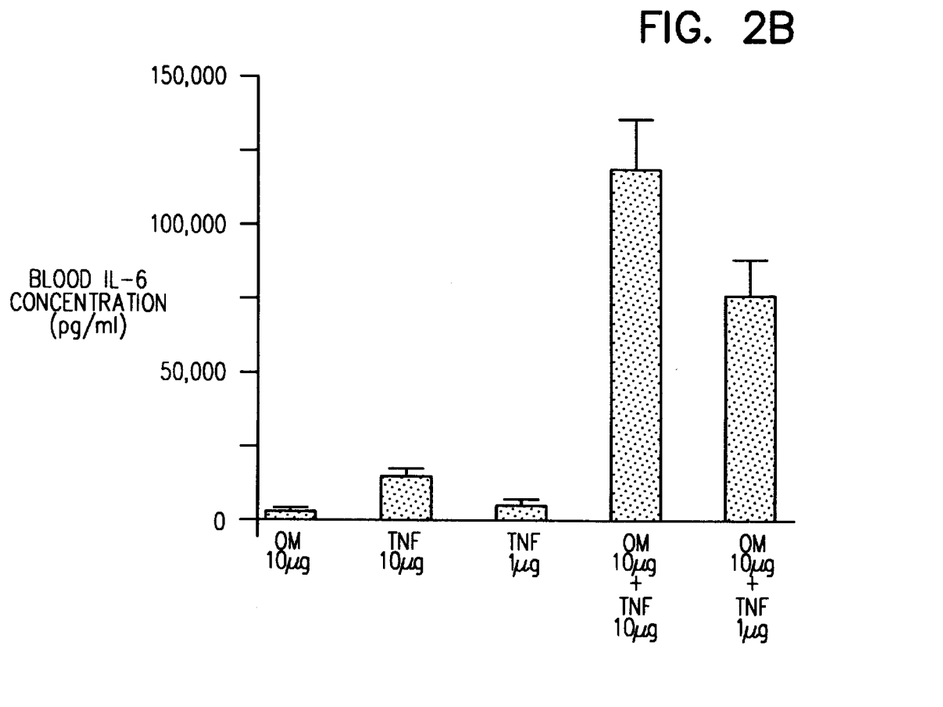

To determine whether the increases in IL-6 were the result of a synergistic or additive effect between Oncostatin M and the TNF produced by LPS, Oncostatin M and either LPS (FIG. 2A) or TNF-α (FIG. 2B) were injected intravenously at the doses shown in FIG. 2. Blood was sampled at 1 hour post injection and assayed for IL-6 by ELISA. The results showed that combinations of Oncostatin M/TNF-α produced significantly higher levels of IL-6 than each cytokine alone and at levels greater than would be expected from just an additive effect (FIG. 2A and 2B). As the dose of TNF-α was a maximally tolerated dose, similar levels of IL-6 could not be attained with TNF-α alone. These findings distinguish Oncostatin M from other TNF-α inhibitors which, when studied in vivo, cause a concordant reduction in both TNF-α and IL-6. In contrast, Oncostatin M reduces TNF-α while increasing IL-6, a second TNF-α antagonist.

The in vivo effects of Oncostatin M were further assessed on the lethality of mice from exposure to LPS. Balb/c mice were injected with 10 μg Oncostatin M intraperitoneally at 4, 2, 1 and 0 (co-injected) hours before LPS challenge. The number of mice surviving to day 7 post LPS was recorded.

As shown in Table 4, the MTD of LPS was increased by Oncostatin M treatment as compared to animals treated with control diluent, as seen in each of three independent studies. Therefore, the altered cascade of cytokines produced by Oncostatin M plus LPS was less toxic than the toxicity due to cytokines produced by LPS alone.

TABLE 6

Effect of Oncostatin M on Survival of Mice following LPS Treatment

| Treatment | Control Diluent (#alive/group total) | Oncostatin M Treatment (#alive/group total) |
| --- | --- | --- |
| 200 μg LPS | 1/15 | 3/15 |
| 100 μg LPS | 1/30 | 19/20 |
| 50 μg LPS | 12/20 | 10/10 |
| 25 μg LPS | 10/10 | 10/10 |

EXAMPLE V

Efficacy of Oncostatin M in Treating Joint Inflammation

This Example describes the beneficial activity of Oncostatin M in a model of antibody-induced joint inflammation in which inflammation occurs in the absence of primary immune response. This allows one to distinguish between two immunoregulatory pathways (immune response and inflammation) which are often interdependent and therefore difficult to separate experimentally.

Figure 3:
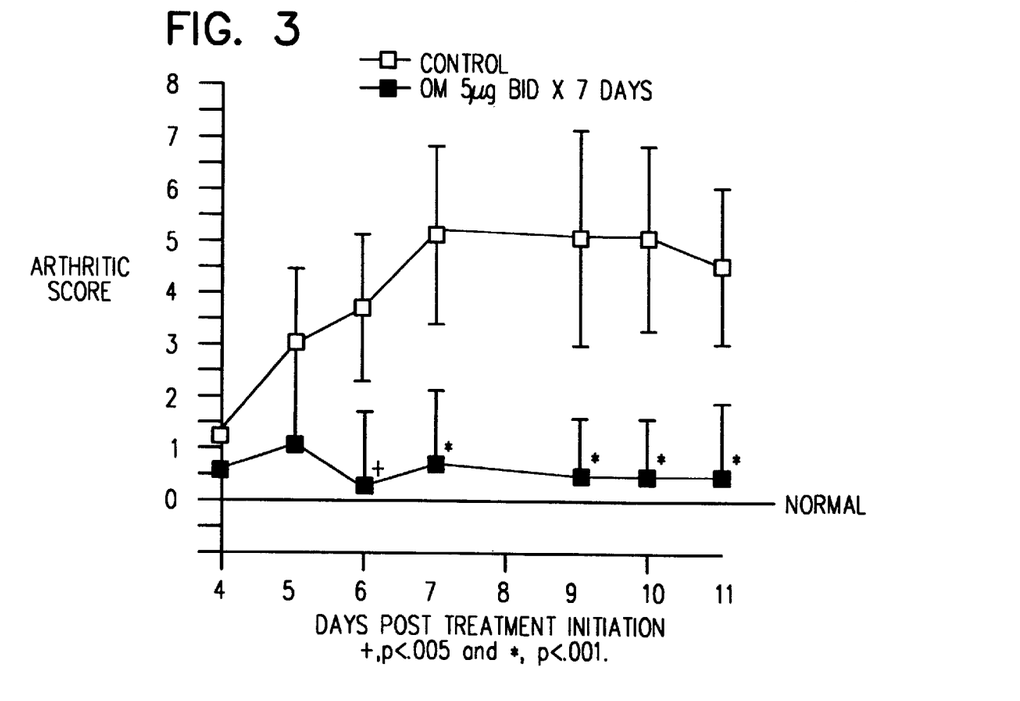
FIG. 3 shows inhibition of joint inflammation by Oncostatin M, where +=$p \leq 0.005$, and * =$p \leq 0.001$.

Groups of 10 Balb/c mice were injected intravenously with a cocktail of 1 mg each of 4 different anti-collagen monoclonal antibodies. At 72 hours, an intravenous boost of 25 μg LPS was given to accelerate the progression of disease. Oncostatin M treatment was initiated at 96 hours, after inflammation was established, and continued for seven days (5 μg, bid). As shown in FIG. 3 the severity of joint inflammation was significantly reduced in Oncostatin M-treated mice compared to control animals when assessed by scales of incidence and severity of arthritis. Importantly, the cessation of treatment was not followed by a delayed onset of inflammation. In two representative joints from Oncostatin M-treated mice and animals treated with control diluent, histological examination showed that treatment with Oncostatin M completely inhibited the influx of inflammatory cells seen in control animals and prevented the tissue damage associated with an inflammatory reaction. The inflammation and tissue injury was quantitated for the rear limbs of the animals. Nine of ten control animals had severe inflammation and tissue injury, with an average score of 26.9±16.2. In contrast only one Oncostatin M-treated mouse had any histological evidence of inflammation with a significantly better score of 2.4±7.6 ($p<0.001$). The findings were consistent in three independent studies.

EXAMPLE VI

Inhibition of EAE by Oncostatin M

This Example describes the inhibition of Experimental Autoimmune Encephalomyelitis (EAE), a murine model of multiple sclerosis and other autoimmune diseases, by Oncostatin M in the absence of immunosuppression. This model shares inflammatory components (proinflammatory cytokines, matrix proteases) with those found in IBD and arthritis models which have been demonstrated to be important mediators of the inflammatory destruction of the neural sheath and progression of the disease state. Importantly, the model provided a means to measure independently the effects of Oncostatin M on the immune and inflammatory components of the disease.

Figure 4:
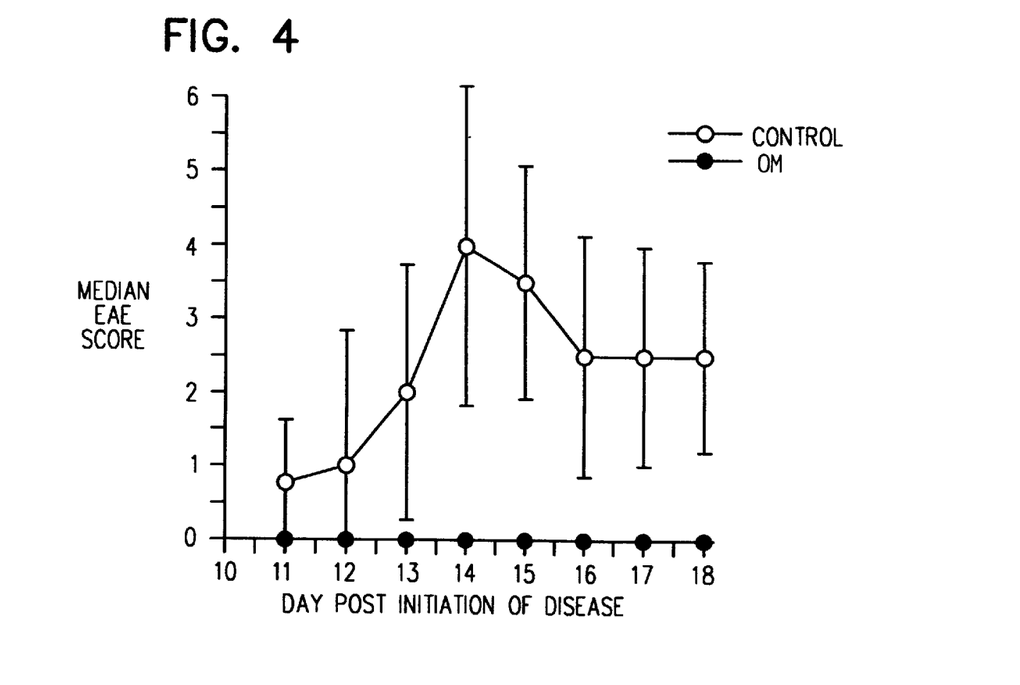
FIG. 4 shows inhibition of EAE by Oncostatin M compared to PBS-treated control animals.

Groups of susceptible mice (B10.S-H2 strain, 10/group) were immunized with a peptide from myelin sheath, proteolipid protein. This peptide contains amino acids 139–151 of proteolipid protein and has previously demonstrated to be encephalogenic (Greer et al., 1996). Following immunization with the peptide in incomplete Freund's adjuvant with 3 mg/ml Myobacterium tuberculosis added) animals received two injections with pertussis toxin. Animals were treated with Oncostatin M (10 μg/day) or control diluent (PBS) on days 4–7 and 12–18. Extent of disease was assessed in a blinded fashion using the following scale: 0-no abnormality; 1-floppy tail with mild hind limb weakness; 2-floppy tail with moderate hind limb weakness; 3-hind leg paresis with or without mild forelimb weakness; 4-hind leg paralysis with or without moderate forelimb weakness; 5-quadriplegia; 6-dead or moribund requiring sacrifice. Shown in FIG. 4 are the median scores of each group ±SD. At day eleven post-immunization, control animals began to exhibit disease symptoms, particularly paralysis. By day 15, nine of the ten animals in the control group had succumbed to the disease. The severity of the disease was also assessed and the disease peaked on day 14 with a median score of 4

(FIG. 4). In contrast, no animal that received treatment with Oncostatin M showed overt signs of the disease in the eighteen days following initiation of the disease. Inhibition of the inflammation associated with this disease was confirmed histologically. Control animals that received diluent had lesions typical of EAE. The majority of the infiltrate was mononuclear cells (mainly T-cells and smaller numbers of macrophages) and a few granulocytes; the infiltrate involved the meninges with extension in a perivascular, white matter orientation. The inflammatory infiltrate was completely absent in Oncostatin M-treated animals.

Figure 5:
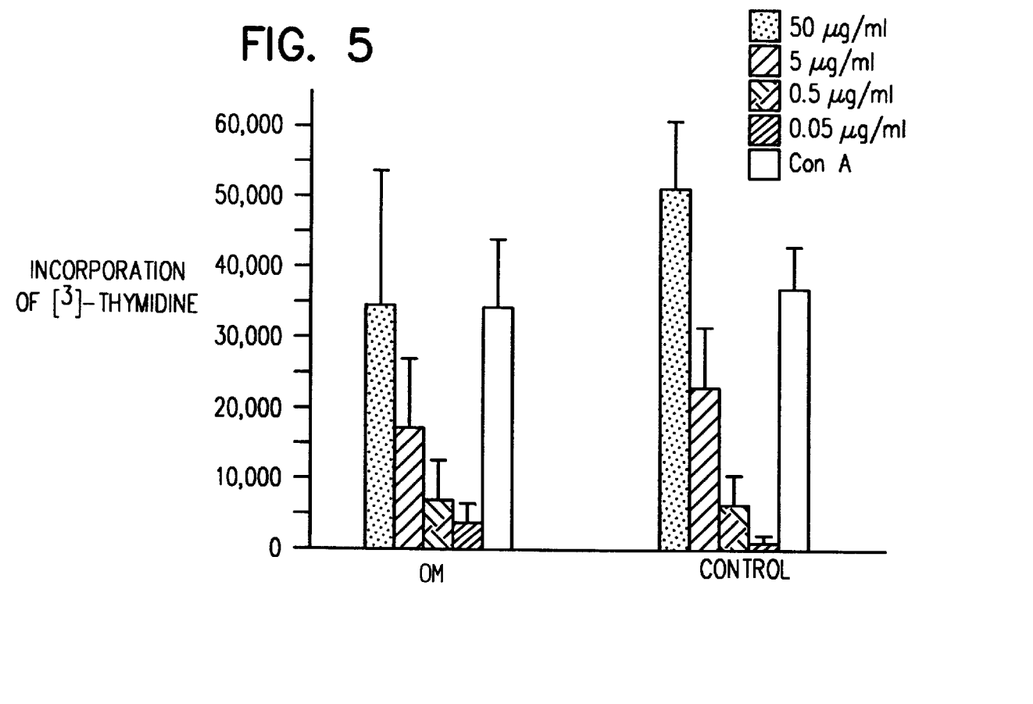
FIG. 5 shows the results from lymph node cell stimulation assay in EAE animals treated with Oncostatin M.

To further examine the mechanism underlying inhibition of the encephalomyelitis, animals were sacrificed on day 18 and the immune response to the proteolipid protein peptide immunization measured. The T-cell response was assessed by measuring proliferative response of the isolated cells to the immunizing peptide in vitro. Lymph node cells were plated at 500,000 cells per well and proteolipid protein peptide was added at the indicated concentrations. Proliferation was measured by ($^3$H)-thymidine incorporation during the final 24 hours of a 4 day culture. Values given are mean cpm (±SD) over control (no peptide stimulus). As shown in FIG. 5, no significant differences were seen in the control and oncostatin M-treated animals. Consistent with this, there was no significant difference in levels of circulating antibodies to the proteolipid protein peptide found in control and Oncostatin M-treated animals. These results indicate that treatment of animals with oncostatin M at levels sufficient to inhibit the inflammatory/degradative aspects of the disease does not suppress normal antibody response.

Figure 6:
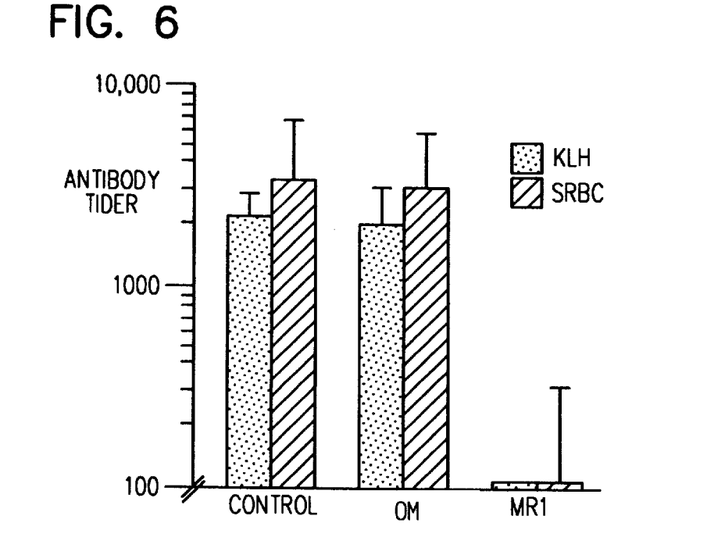
FIG. 6 shows the immune response to a T-cell dependent antigen in mice receiving Oncostatin M.

Results of an additional study similarly demonstrate that Oncostatin M treatment does not modify the immune response to either of two T-cell dependent antigen keyhole limpet hemocyanin (KLH) or sheep red blood cells (SRBC) (FIG. 6). Balb/C mice were injected with 1×10$^8$ SRBC i.v. or 250 μg KLH i.p. on day 0 then treated with Oncostatin M (30 μg, i.v., days 0–10), PBS (100 μl i.v., days 0–10) or MR1 (200 μg i.v. days 0, 2, and 4)). Mice were bled at seven day intervals and assayed for titers to SRBC or KLH by ELISA.

Oncostatin M is thus distinguished from compounds that are ligand antagonists and are anti-inflammatory primarily because they are immunosuppressive and do modify T cell and B cell responses to antigen. Oncostatin M is anti-inflammatory and not immunosuppressive.

EXAMPLE VII

Expression of Human Oncostatin M Derivatives in *Pichia pastoris*

This Example describes the expression in the yeast *Pichia pastoris* of several recombinant derivatives of human Oncostatin M, the fermentation and purification of said Oncostatin M derivatives, and the demonstration of the in vivo and in vitro efficacy of a PiOM derivative engineered to eliminate one N-linked and two potential O-linked glycosylation sites (PiOM-194[TKO]).

The Pichia gene expression system offers several advantages for the efficient production of recombinant proteins, including: 1. Use of a strong inducible promoter (alcohol oxidase-1; AOX-1) that offers the potential for high expression levels (~30% of total protein, with secretion in the gram/liter range seen for some recombinant proteins. 2. Yeast have post-translational modification capabilities including proteolytic processing, protein refolding, and carbohydrate addition. In contrast to *S. cerevisiae,* this strain of yeast rarely hyperglycosylates proteins. 3. High cell-density fermentation has been demonstrated in a simple, well-defined medium. 4. Potentially simplified purification process due to simple, well-defined medium and limited secretion of host cell proteins.

Figure 7:
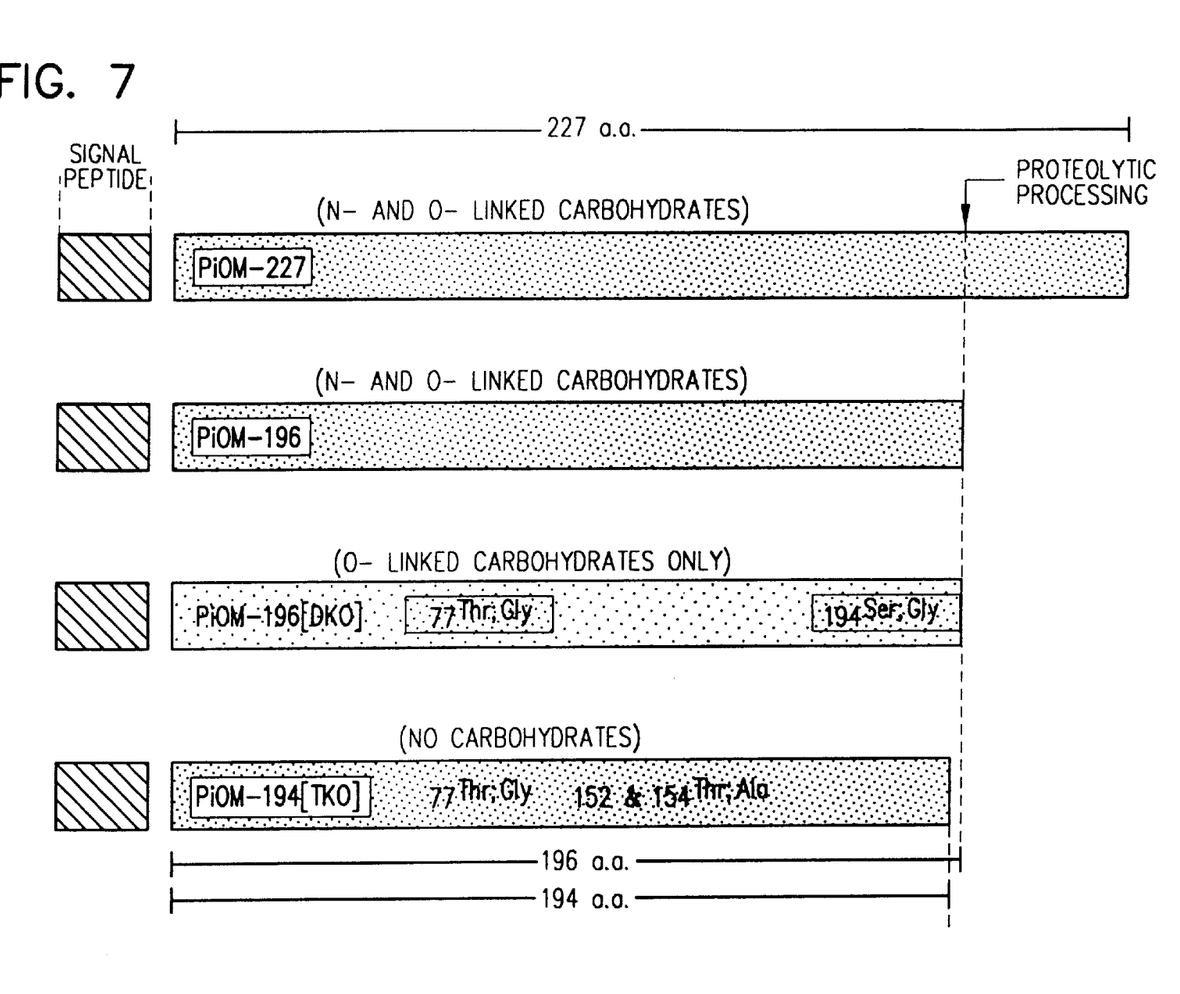
FIG. 7 shows Oncostatin M forms produced in *Pichia pastoris*.

Four different oncostatin M proteins were produced in Pichia as represented in FIG. 7. Desired mutations were engineered into a human Oncostatin M cDNA; these Oncostatin M derivatives were subcloned downstream of and in frame with an α-mating factor leader sequence to facilitate efficient protein secretion. These constructs were further subcloned into a homologous recombination vector (pPIC9) such that they were under the transcriptional control of the methanol inducible AOX-1 promoter. Each plasmid was then transfected into *P. pastoris* to permit its overexpression. Transcription from the inducible promoter was derepressed by addition of methanol which, consequently, resulted in high protein expression levels. The vectors were designed to secrete the following four PiOM derivatives: 1. Full length pro-Oncostatin M of 227 amino acids (PiOM-227); 2. Mature 196 amino acid form (PiOM-196); 3. A 196 amino acid form with two potential N-linked glycosylation sites mutated to eliminate asparagine-linked glycosylation (PiOM-196[DKO]); and 4. Mature 194 amino acid form with three potential glycosylation sites mutated to further reduce yeast glycosylation (PiOM-194[TKO]).

For fermentation and purification, a four-day fermentation of the fourth construct, PiOM-194[TKO], achieved an optical density $A_{600}$ of 285 and a wet cell weight of 345 gm/L. The PiOM titers, based on ELISA, were 144 mg/L within 5.5 hours post-induction and reached a final titer of 763 mg/L prior to termination of the reactor run. This four-day fermentation generated a total of 0.9 gm of PiOM-194[TKO] in a volume of 1.5 L of supernatant. The protocol used for the purification of PiOM-194[TKO] was the same as that employed for the first three forms of PiOM (PiOM-227, PiOM-196, and PiOM-196[DKO]). A 2-step protocol comprising cation exchange chromatography at low pH followed by reverse-phase HPLC yielded greater than 95% homogeneity for the first three forms. Results of this initial purification protocol with PiOM-194[TKO] showed in the final preparation there were two Oncostatin M bands (by SDS-polyacrylamide gel electrophoresis), a preliminary evaluation in vivo in mice showed this material to be suitably active.

Characterization of CHO-OM and Pichia-derived Oncostatin M protein from the first three constructs (i.e. PiOM-227, PiOM-196, and PiOM-196[DKO]) indicated that: (1) a significant amount of C-terminal heterogeneity was associated with the PiOM-227 protein, (2) Oncostatin M produced from CHO or Pichia is processed to a mature form of 194 or 195 amino acids, (3) Pichia forms of Oncostatin M contain O-linked carbohydrate chains composed primarily of mannose oligosaccharide(s), and (4) only one of the two potential sites for N-linked glycosylation encoded within the Oncostatin M gene was glycosylated by yeast cells (i.e. Asparagine 75).

Although equally active in vitro, PiOM-196[DKO] was 10 to 30 fold less active than CHO-OM in vivo in mice. This was not due to the absence of N-linked glycosylation as non-glycosylated bacterial expressed Oncostatin M was equally active to glycosylated OM in mice. The PiOM also had reduced in vivo activity approximately three to four fold less than that of CHO-OM in inducing platelets in primates (Cynomolgus monkeys). A decreased activity of the first three Pichia Oncostatin M constructs in mice was likely due to an accelerated clearance. This was produced due to carbohydrates of the proteins as it could be blocked by mannan, a carbohydrate receptor antagonist. Consequently, the fourth homologous recombination vector was constructed to encode a mature form of Oncostatin M in which mutations to one N- and two O-linked glycosylation sequences were incorporated to produce a protein with reduced glycosylation. To determine in vivo clearance of PiOM-194[TKO] compared to CHO-OM, each form (200 μg) was injected i.v. via a tail vein into C3H/HeJ mice (3 mice/time point). Mice were bled from the retro-orbital sinus and plasma samples collected at time points over 60 min. Plasma concentrations of Oncostatin M were determined by comparison to a standard curve using an OM-specific ELISA. Control studies showed no interference in measurement occurred in the presence of plasma. The plasma concentrations of PiOM-194[TKO] were found to be equivalent to the CHO-OM.

IL-6 induction in mice was selected as an in vivo assay to evaluate preparations of Oncostatin M because there is a good dose response, results are consistent and reproducible, and the assay is rapid. C3H/HeJ mice (three per group) were injected i.v. with Oncostatin M preparations and bled via the retro-orbital sinus 60 minutes later. Serum samples were evaluated for murine IL-6 levels using the Endogen mini kit. Protein from this fourth construct, PiOM-194[TKO], had activity comparable to CHO-OM in inducing IL-6 in mice. CHO-OM and PiOM-194[TKO] at 30, 10, and 3 μg were each comparable in inducing IL-6 in mice. The third construct, PiOM-196[DKO], was included at 30 μg and results confirmed earlier findings that PiOM-196[DKO] was ~10-fold less active that PiOM-194[TKO] and CHO-OM.

The efficacy of PiOM-194 [TKO] in the treatment of gastrointestinal inflammation was determined. Swiss-Webster mice were treated with dextran sodium sulfate (DSS) as described in Example I and a comparison was made of the efficacy of CHO-OM and PiOM-194[TKO]. CHO-OM was dosed at 10 μg per day i.p. for the duration of the study (10 days) and PiOM-194[TKO] with the same schedule at 3, 10, or 30 μg. Groups of five mice were treated with DSS and the indicated treatment. Treatment was initiated 1 day following DSS and continued until the day of sacrifice (day 10). As shown in Table 7, both Oncostatin M proteins were highly effective in blocking both the injury and inflammation associated with this disease.

method. The modified 194 amino acids Oncostatin M cDNA was cloned into the pD16 expression vector. pD16 is a derivative of the plasmid pcDNA3 (InVitrogen) modified as follows: The neomycin resistance gene from pcDNA3 was replaced with the murine dihydrofolate reductase (DHFR) gene under control of the enhancerless SV40 promoter (also referred to as the "weakened DHFR"; note that only the promoter was weakened, not the DHFR enzyme). The enhancerless promoter still contains the SV40 origin of replication, so can be used in transient COS transfections. The Oncostatin M gene is expressed from the CMV promoter, and the polyadenylation signal is from the bovine growth hormone gene. The expression cassette for the Oncostatin M is flanked by transcription termination sequences (i.e., 5' to the promoter and 3' to the polyA site). The vectors contain two distinct restriction site polylinkers, one 3' to the promoter for cloning the gene of interest, and one 5' to the promoter for vector linearization prior to transfection. The ampicillin resistance gene and ColE1 origin are included for plasmid propagation in *E. coli*.

The fully processed 194 amino acids form of Oncostatin M preceded by simian TGFβ signal peptide was assembled in the expression vector. TGFβ signal peptide was processed during oncostatin M secretion. The transfection using this vector produced high expressing cell lines and the expressed recombinant protein was fully processed.

The CHO cells that produce Oncostatin M were grown in an Applikon 3 L stirred tank reactor using a serum and bovine product free, basal medium of PF-CHO (JRH Biosciences) supplemented with 500 ng/ml insulin, 4 mM L-glutamine, and 1.5 μM methotrexate. The medium was seeded at approximately $1.5 \times 10^5$ cells/ml. The culture was maintained with a daily bolus of 10× ERDF formulation (Gibco, enriched RPMI DMEM F12) and harvested at day 12 with the cells at 64% viability. Final concentration of Oncostatin M determined by ELISA was approximately 400 μg/ml.

Oncostatin M was purified from the culture supernatant using anion exchange and cation exchange chromatography. An additional, final anion exchange chromatography step was utilized to lower the endotoxin level to <1 EU/mg.

The aforementioned Examples demonstrate that Oncostatin M has a spectrum of anti-inflammatory properties in vitro and in vivo that suggests a significant therapeutic

TABLE 7

| Treatment | | Proximal | Middle | Distal | Cumulative |
|---|---|---|---|---|---|
| | | Mean Regional and Cumulative Injury Scores | | | |
| Pi-OM(TKO) | 30 μg | $0.80 \pm 0.17^a$ | $2.00 \pm 0.51^b$ | $2.70 \pm 1.18^b$ | $1.83 \pm 0.45^b$ |
| Pi-OM(TKO) | 10 μg | $1.65 \pm 0.44^a$ | $2.55 \pm 0.56^b$ | $4.30 \pm 0.91^b$ | $2.83 \pm 0.46^b$ |
| Pi-OM(TKO) | 3 μg | $1.25 \pm 0.60^a$ | $2.60 \pm 0.65^b$ | $3.75 \pm 1.91^b$ | $2.53 \pm 0.71^b$ |
| CHO-OM | 10 μg | $3.15 \pm 0.60^b$ | $3.15 \pm 0.60^b$ | $5.42 \pm 1.77^b$ | $3.22 \pm 0.75^b$ |
| DSS Control | | $5.98 \pm 0.93$ | $10.36 \pm 1.11$ | $12.64 \pm 1.00$ | $9.66 \pm 0.72$ |
| | | Mean Regional and Cumulative Inflammatory Scores | | | |
| Pi-OM(TKO) | 30 μg | $0.85 \pm 0.50^a$ | $2.88 \pm 1.51$ | $2.05 + 1.28^a$ | $1.93 \pm 0.67^b$ |
| Pi-OM(TKO) | 10 μg | $1.55 \pm 0.28$ | $3.75 \pm 0.93$ | $3.12 \pm 0.63$ | $2.80 \pm 0.43^b$ |
| Pi-OM(TKO) | 3 μg | $2.10 \pm 1.35$ | $3.30 \pm 1.10$ | $1.90 \pm 0.83^a$ | $2.43 \pm 0.62^b$ |
| CHO-OM | 10 μg | $1.70 \pm 0.54$ | $3.45 \pm 0.58$ | $2.57 \pm 0.74$ | $2.57 \pm 0.39^b$ |
| DSS Control | | $4.91 \pm 0.61$ | $6.00 \pm 0.49$ | $5.52 \pm 0.54$ | $5.48 \pm 0.32$ |

EXAMPLE VIII

An Oncostatin M producing cell line was generated by transfecting CHO DG44 cells with expression vector encoding human Oncostatin M using the high copy electroporation opportunity for the molecule in the treatment of, among other things, IBD, multiple sclerosis, and rheumatoid arthritis. Oncostatin M significantly reduced the levels of both injury and inflammation in the DSS-induced murine colitis model of IBD. Importantly, this efficacy was demonstrated using either i.v. or oral modes of treatment. Oncostatin M has demonstrated significant protection against inflammation and GI damage caused by anticancer chemotherapy and irradiation. In additional models of disease with inflammatory mediators common to IBD, Oncostatin M significantly reduced the levels of inflammation and joint destruction in the antibody induced arthritis model of arthritis, and neural sheath destruction and paralysis in the EAE model of multiple sclerosis. Importantly, Oncostatin M administered at therapeutic levels does not suppress normal antibody response to exogenous antigen and, therefore, offers a therapeutic approach to inflammation which is significantly different from that of other biomolecules currently being developed. Moreover, the effective dose of Oncostatin M used in animal models of inflammatory disease caused no detectable toxicity, and preliminary data suggest a significant (>10-fold) therapeutic window between effective dose and toxicity.

Although the foregoing invention has been described in some detail by way of illustration and example for purposes of clarity of understanding, it will be obvious that certain changes and modifications may be practiced within the scope of the appended claims.

What is claimed is:

1. A method for inhibiting gastrointestinal inflammation in a mammalian host comprising administering to the host a gastrointestinal inflammation-inhibiting amount of Oncostatin M.

2. The method of claim 1, wherein said host suffers from or is susceptible to acute gastrointestinal inflammation.

3. The method of claim 1, wherein said host suffers from or is susceptible to chronic gastrointestinal inflammation.

4. The method of claim 1, wherein said Oncostatin M is administered orally.

5. The method of claim 1, wherein said Oncostatin M is human oncostatin M.

6. The method of claim 5, wherein said human Oncostatin M is expressed in a mammalian cell line.

7. The method of claim 6, wherein the mammalian cell line is CHO.

8. The method of claim 5, wherein said human Oncostatin M is expressed in yeast.

9. The method of claim 8, wherein said yeast is Pichia.

10. The method of claim 1, wherein said gastrointestinal inflammation is associated with Crohn's Disease.

11. The method of claim 1, wherein said gastrointestinal inflammation is associated with ulcerative colitis.

12. The method of claim 1, wherein said gastrointestinal inflammation is associated with inflammatory bowel disease.

* * * * *